(12) United States Patent
Lin et al.

(10) Patent No.: US 7,846,099 B2
(45) Date of Patent: Dec. 7, 2010

(54) APPARATUS, SYSTEM, AND METHOD FOR PROVIDING A CONTINUOUS SCANNING SEQUENCE FOR ULTRASOUND IMAGING

(75) Inventors: Feng Lin, Niskayuna, NY (US); Christopher Robert Hazard, Niskayuna, NY (US); David Thomas Dubberstein, Waukesha, WI (US); Steven Charles Miller, Waukesha, WI (US)

(73) Assignee: General Electric Company, Niskayuna, NY (US)

( * ) Notice: Subject to any disclaimer, the term of this patent is extended or adjusted under 35 U.S.C. 154(b) by 1080 days.

(21) Appl. No.: 11/551,755

(22) Filed: Oct. 23, 2006

(65) Prior Publication Data

US 2008/0146920 A1      Jun. 19, 2008

(51) Int. Cl.
*A61B 8/00* (2006.01)
(52) U.S. Cl. .................... 600/447; 600/443
(58) Field of Classification Search ............. 600/437, 600/443, 447; 382/128
See application file for complete search history.

(56) References Cited

U.S. PATENT DOCUMENTS

| | | | |
|---|---|---|---|
| 4,888,694 A | 12/1989 | Chesarek | |
| 4,993,417 A | 2/1991 | Seo | |
| 5,501,223 A | 3/1996 | Washburn et al. | |
| RE35,371 E | 11/1996 | Seo | |
| 5,709,209 A | 1/1998 | Friemel et al. | |
| 6,221,020 B1 | 4/2001 | Lysyansky et al. | |
| 6,390,980 B1 | 5/2002 | Peterson et al. | |
| 2007/0088215 A1* | 4/2007 | Dubberstein et al. | 600/437 |

* cited by examiner

*Primary Examiner*—Eric F Winakur
*Assistant Examiner*—Katherine L Fernandez
(74) *Attorney, Agent, or Firm*—Jason K. Klindtworth

(57) ABSTRACT

A method of performing a scanning sequence for an ultrasound scan includes establishing a number of ultrasound beams to be transmitted during an ultrasound scan, establishing a pulse repetition interval to be used for performing the ultrasound scan, and establishing a number of firings of each of the ultrasound beams to be performed during the ultrasound scan. The method further includes performing a scanning sequence based on a processing of one or more parameters selected from the group consisting of the number of ultrasound beams, the pulse repetition interval, and the number of firings of the ultrasound beams, wherein the processing of the one or more parameters is configured to provide a continuous interleaving in the transmitted beams thereby avoiding a generation of beam interleaving discontinuities and a formation of artifacts in a resulting image.

19 Claims, 4 Drawing Sheets

APPARATUS, SYSTEM, AND METHOD FOR PROVIDING A CONTINUOUS SCANNING SEQUENCE FOR ULTRASOUND IMAGING

FIELD OF THE INVENTION

Embodiments of the present invention are generally related to imaging systems, and, more particularly, to a continuous scanning sequence for ultrasound imaging.

BACKGROUND OF THE INVENTION

In ultrasound imaging modes such as elasticity, strain, color-flow, and B-flow wherein tissue or flow motion needs to be detected, multiple firings of beams are performed to extract motion information from received signals that typically include a relatively high signal-to-noise ratio. In such modes, a minimum time interval is required between repeated firings of the same beam to allow sufficient displacement of tissue or flow being measured. When the motion or displacement to be measured occurs relatively slowly, more time is needed between firings to obtain a measurable difference in received echo phase. This minimum motion or displacement time is often more than a multiple of the minimum time needed to receive echoes from a maximum image depth, and/or the minimum time needed so that echoes from a first firing are attenuated sufficiently so that these echoes will not interfere with echoes from a second firing. Accordingly, for an example minimum motion or displacement time interval of 1 unit, a pulse repetition interval (PRI) should be greater than 1.

Typically, a minimum motion or displacement time interval may be so long that a frame rate of acquired images may become undesirably long, especially if transmitting all the firings of one beam consecutively. Accordingly, interleaving of beam firings is typically used to increase a frame rate of acquired images. Such interleaving is typically accomplished by firing multiple different beams within a time interval, such as a PRI, between two consecutive firings of at least one of the beams.

In conventional ultrasound elasticity, color flow, or B-flow imaging techniques, interleaving groups using multiple beam firings are commonly used. FIG. 1 depicts a prior art scanning sequence 10 using interleaving groups. The beams used in the scanning sequence 10 are represented by a letter designation 16, such as A, B, C . . . etc. Beam firings are designated by a firing index number 18, such as 1, 2, 3 . . . etc. A firing sequence 20 is indicated by arrow 22 traversing a set of firing indices and a number of the sequence is indicated by a superscript 24.

If a PRI between firings of beam A is desired to be a certain amount (e.g., a PRI of five) so that N−1 beams (e.g., four) can be inserted in between, typical practice is to group N beams into one group 12, transmit the first firings (indicted by the firing index 1 24 for each of the beams 12) of the N beams sequentially during the first PRI, and then, during a next PRI, transmit the second firings of the N beams, etc., until all the firings are transmitted. As indicted in FIG. 1, the first firings of beams A-E are sequentially transmitted, followed by the second firings of beams A-E, etc., until a desired number of firings of each of the beams is reached (such as four firings, as indicated in FIG. 1). Then, another group 14 of beams is transmitted in the same manner until the desired number of firings is reached. However, this technique generates beam interleaving discontinuities between groups, causing formation of artifacts in a resulting image. Such artifacts may be especially pronounced in tissue elasticity imaging when interleaving groups are used.

BRIEF DESCRIPTION OF THE INVENTION

In an example embodiment, the invention includes a method of performing a scanning sequence for an ultrasound scan. The method includes establishing a number of ultrasound beams to be transmitted during an ultrasound scan, establishing a pulse repetition interval to be used for performing the ultrasound scan, and establishing a number of firings of each of the ultrasound beams to be performed during the ultrasound scan. The method also includes performing a scanning sequence based on a processing of one or more parameters selected from the group consisting of the number of ultrasound beams, the pulse repetition interval, and the number of firings of the ultrasound beams, wherein the processing of the one or more parameters is configured to provide a continuous interleaving in the transmitted beams thereby avoiding a generation of beam interleaving discontinuities and a formation of artifacts in a resulting image.

In another example embodiment, the invention includes an apparatus for performing a scanning sequence for an ultrasound scan. The apparatus includes a first module for establishing a number of ultrasound beams to be transmitted during an ultrasound scan, a second module for establishing a pulse repetition interval to be used for performing the ultrasound scan, and a third module for establishing a number of firings of each of the ultrasound beams to be performing during the ultrasound scan. The apparatus also includes a fourth module for performing a scanning sequence based on a processing of one or more parameters selected from the group consisting of the number of ultrasound beams, the pulse repetition interval, and the number of firings of the ultrasound beams, wherein the processing of the one or more parameters is configured to provide a continuous interleaving in transmitted ultrasound beams thereby avoiding a generation of beam interleaving discontinuities and a formation of artifacts in a resulting image.

In another example embodiment, the invention includes a system for performing a scanning sequence for an ultrasound scan. The system includes a transmitter for transmitting ultrasound beams to a subject during an ultrasound scan, a receiver for receiving echo signals from the subject responsive to transmitted ultrasound beams and a memory for storing information corresponding to the echo signals. The system also includes a controller for performing a scanning sequence based on a processing of one or more parameters selected from the group consisting of the number of ultrasound beams, the pulse repetition interval, and the number of firings of the ultrasound beams, wherein the processing of the one or more parameters is configured to provide a continuous interleaving in transmitted beams thereby avoiding a generation of beam interleaving discontinuities and a formation of artifacts in a resulting image.

In another example embodiment, the invention includes computer readable media containing program instructions for performing a scanning sequence for an ultrasound scan. The computer readable media includes a computer program code for establishing a number of ultrasound beams to be transmitted during an ultrasound scan, a computer program code for establishing a pulse repetition interval to be used for performing the ultrasound scan, and a computer program code for establishing a number of firings of each of the ultrasound beams to be performing during the ultrasound scan. The media also includes a computer program code for performing a scanning sequence based on a processing of one or more parameters selected from the group consisting of the number of ultrasound beams, the pulse repetition interval, and the number of firings of the ultrasound beams, wherein the processing of the one or more parameters is configured to provide a continuous interleaving in transmitted ultrasound beams thereby avoiding a generation of beam interleaving discontinuities and a formation of artifacts in a resulting image.

DETAILED DESCRIPTION OF THE INVENTION

Figure 1:
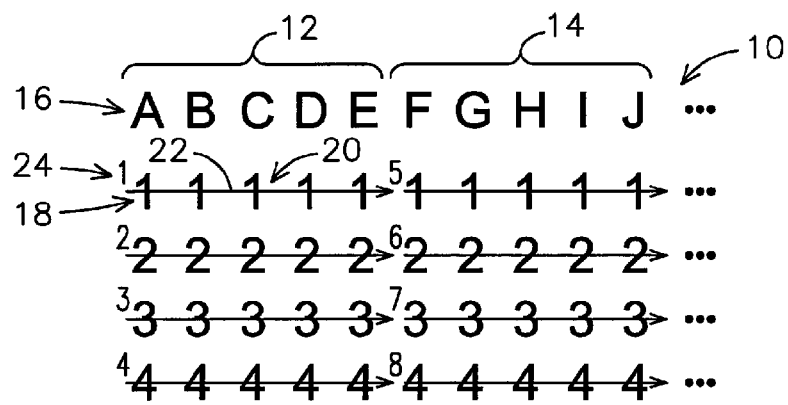
FIG. 1 shows a prior art scanning sequence for an ultrasound scan.
Figure 2:
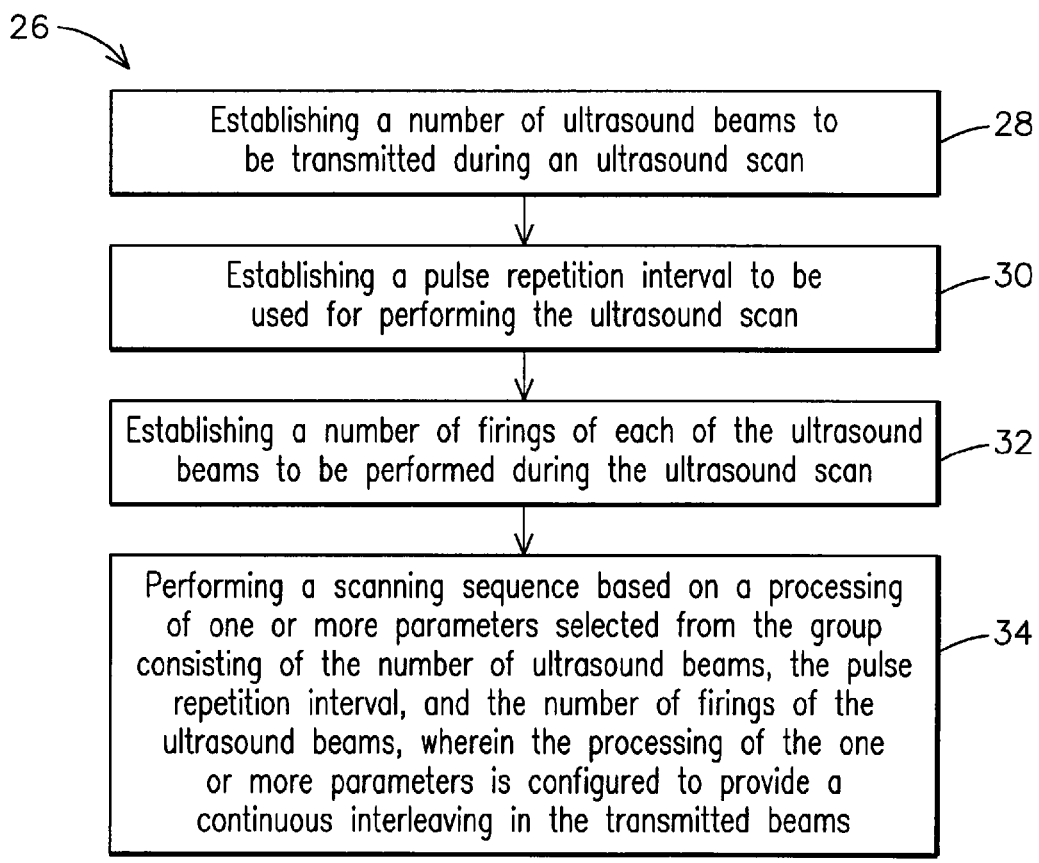
FIG. 2 shows an example block diagram of a method for controlling a scanning sequence for an ultrasound scan according to an embodiment of the invention.

The inventors have developed an innovative ultrasound scanning sequence that provides a continuous interleaving in transmitted ultrasound beams for avoiding a generation of beam interleaving discontinuities and a formation of artifacts in a resulting image. In an embodiment, the scan sequence is configured to repeat a same order of firings, such as by applying the same firing sequence, and to fire different beams for each firing. Accordingly, as shown in the block diagram 26 of FIG. 2, an example method for providing a continuous ultrasound scanning sequence includes establishing a number of ultrasound beams to be transmitted during an ultrasound scan 28, establishing a pulse repetition interval to be used for performing the ultrasound scan 30, and establishing a number of firings of each of the ultrasound beams to be performed during the ultrasound scan 32. The method further includes performing a scanning sequence 34 based on a processing of one or more parameters selected from the group consisting of the number of ultrasound beams, the pulse repetition interval, and the number of firings of the ultrasound beams. The processing of the one or more parameters may be configured to provide a continuous interleaving in the transmitted beams, thereby avoiding a generation of beam interleaving discontinuities and a formation of artifacts in a resulting image. The scanning sequence method may be used in ultrasound imaging modes that require multiple beam firings, such as used in tissue elasticity imaging.

In an embodiment of the invention, performing the scanning sequence may include establishing respective firing indices corresponding to the number of firings of each of the ultrasound beams, and controlling firing of each of the ultrasound beams according to the firing indices. Controlling firing of each of the ultrasound beams may include changing a firing index and an ultrasound beam to be fired for each firing to be performed. In an embodiment, changing an ultrasound beam to be fired may include changing to a different beam, such as an adjacent beam. Changing the firing index may include incrementing or decrementing the firing index.

The method may further include repeating the process of changing a firing index and an ultrasound beam to be fired until each firing index for each of the ultrasonic beams has been fired. In another aspect of the invention, the scanning sequence may be arranged into a plurality of firing sequences, each firing sequence comprising the number of firings. The firing index may be reset to the same initial index at a beginning of each respective firing sequence. In yet another aspect of the invention, dummy beams and/or dummy firing indices may be used to provide temporal placeholders for the scanning sequence. In another embodiment, the scanning sequence may include wrapping the scanning sequence from at least a first beam to be fired in the scanning sequence to at least a last beam to be fired in the scanning sequence.

Figure 3:
FIG. 3 shows an example scanning sequence for an ultrasound scan according to an embodiment of the invention.

FIG. 3 shows an example scanning sequence according to the above described method wherein the number of firings is four and the PRI is five. The scanning sequence includes dummy beams 38 that used as temporal placeholders during a portion of the scanning sequence 36. The dummy beams 38 may include beams that are actually fired, but not used in later processing, or may be simulated to provide one or more temporal firing placeholders used during the scanning sequence 36. As shown in FIG. 3, the scanning sequence 36 includes changing a beam and a firing index for each firing during a firing sequence 40. For example, the firing sequence 40 may include firing a first firing of beam A, a second firing of a first dummy beam 42, a third firing of a second dummy beam 44, and a fourth firing of a third dummy beam 46, thereby establishing a firing number of 4. A second firing sequence 48 may include firing a first firing of beam B, a second firing of beam A, a third firing of a first dummy beam 42, and a fourth firing of a second dummy beam 44. In this manner, a PRI between firings of sequential firing indexes of a beam is established. For example, the above described scanning sequence results in a PRI of five because there are five firings from a first firing of a beam, such as beam A, until a second firing of the same beam. The firing sequences are repeated in the above manner until the firings for each of the beams in the scanning sequence 36 are performed.

Figure 4:
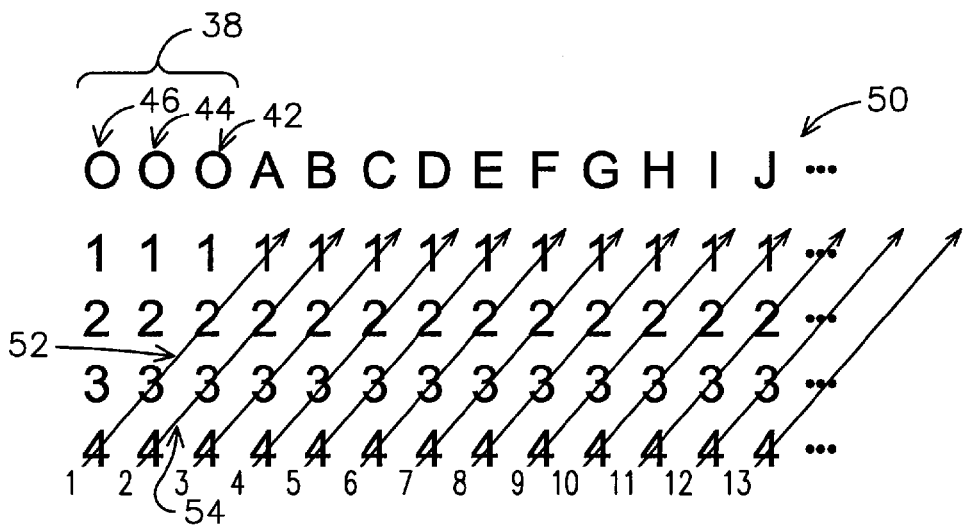
FIG. 4 shows another example scanning sequence for an ultrasound scan according to an embodiment of the invention.

By changing an order of the firings in the scanning sequence 36 shown in FIG. 3, a different PRI may be obtained. FIG. 4 shows an example scanning sequence 50 wherein the number of firings is four and the PRI is three. A first firing sequence 52 may include firing a forth firing of third dummy beam 46, a third firing of a second dummy beam 44, a second firing of a first dummy beam 42, and a first firing of a beam A to establish a firing number of four. A second firing sequence 54 may include firing a forth firing of second dummy beam 44, a third firing of a first dummy beam 42, a second firing of beam A, and a first firing of a beam B. The scanning sequence 50 shown in FIG. 4 results in a PRI of three because there are three firings from a one firing of a beam, such as beam A, until a next firing of the same beam. The firing sequences are repeated in the above manner until the firings for each of the beams in the scanning sequence 50 are performed, thereby achieving continuous scanning.

Figure 5:
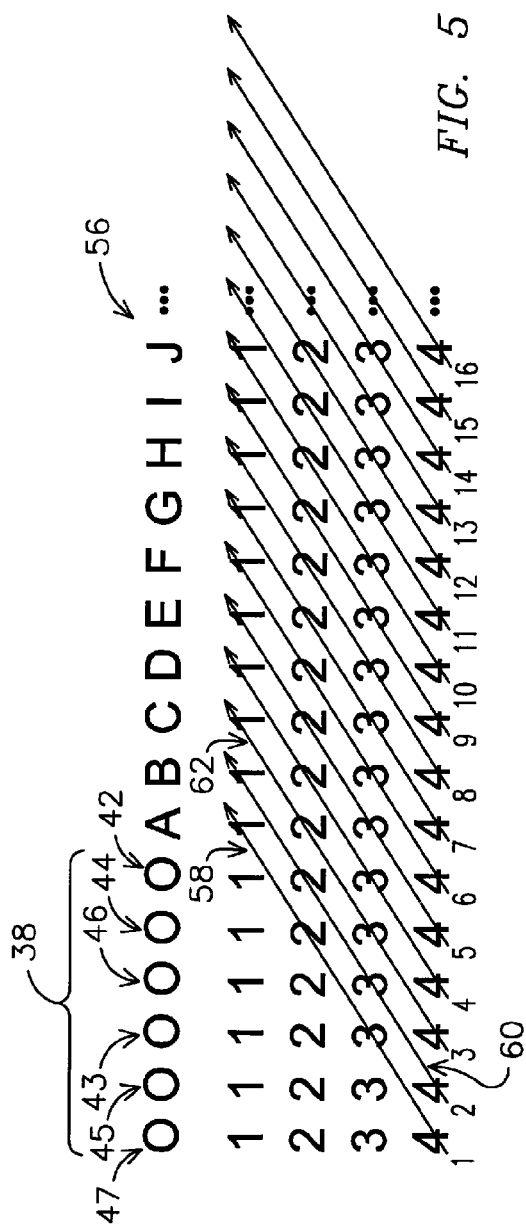
FIG. 5 shows another example scanning sequence for an ultrasound scan according to an embodiment of the invention.

A PRI may be increased by sequentially firing every other beam, or more, in a firing sequence. FIG. 5 shows an example scanning sequence 56 wherein the number of firing is four and a PRI is seven. Additional dummy beams, such as a forth 43, fifth 45, and sixth 47 dummy beams, may need to be added to provide temporal placeholders according to a number of beams to be skipped. As shown, a first firing sequence 58 may include firing a forth firing of sixth dummy beam 47, a third firing of a forth dummy beam 43, a second firing of a second dummy beam 44, and a first firing of a beam A to establish a firing number of 4. A second firing sequence 60 may include firing a forth firing of fifth dummy beam 45, a third firing of third dummy beam 46, a second firing of first dummy beam 42, and a first firing of a beam B. A third firing sequence 62 may include firing a forth firing of forth dummy beam 43, a third firing of second dummy beam 44, a second firing of beam A, and a first firing of a beam C. In this manner a PRI of seven between firings of sequential firing indexes of a beam is established.

As shown in the above examples, a continuous scanning sequence according to the inventions can be implement for a desired PRI according to the equation 1:

$$PRI = n*f \pm 1, \qquad 1)$$

where f is a number of firings, n is any non-negative integer.

To implement other PRIs that may not be able to be represented by equation 1, a time interval between firings may be adjusted at the same time that interleaving is performed. For example, to implement the case of a number of firings equal to four with a PRI of six, the same firing sequence as shown in FIG. 3 (e.g., number of firings=4 and PRI=5) may be used by increasing a time interval between firings to 1.2 times.

Figure 6:
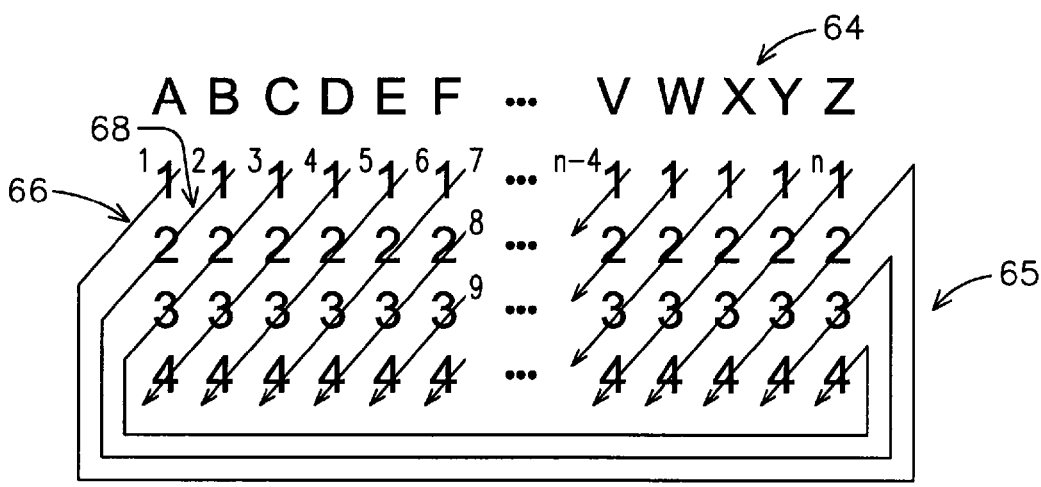
FIG. 6 shows another example scanning sequence for an ultrasound scan according to an embodiment of the invention.

FIG. 6 shows an example of scanning sequence 64 that wraps around one or more scanning sequence, such as wrapping around scanning sequences 64 of adjacent frames, so that no dummy beam is needed as a temporal placeholder. As shown in FIG. 6, the scanning sequence 64 includes changing a beam and a firing index for each firing during a firing sequence 66 and wrapping around to an end 65 of the scanning sequence 64 when necessary to complete the sequence 64. For example, the firing sequence 66 may include firing a first firing of beam A, a second firing of beam Z, a third firing of beam Y, and a fourth firing of beam X to establish a firing number of four. A second firing sequence 68 may include firing a first firing of beam B, a second firing of beam A, a third firing of beam Z, and a fourth firing of beam Y. The beams A, B, C . . . and beams . . . X, Y, Z may belong to adjacent scanning sequence frames, and the adjacent frames may then be seamlessly connected without using dummy beams. This scanning sequence 64 results in a PRI of five. The firing sequences are repeated in the above manner periodically until scanning is stopped.

Figure 7:
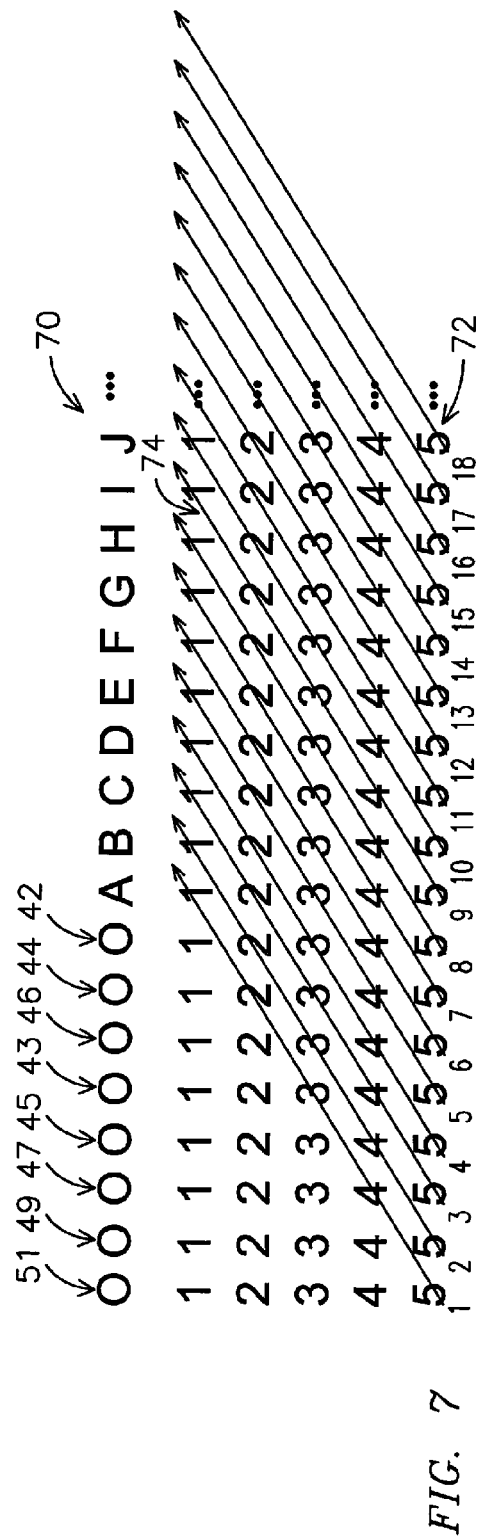
FIG. 7 shows another example scanning sequence for an ultrasound scan according to an embodiment of the invention.

FIG. 7 shows a scanning sequence 70 wherein at least one dummy firing 72 is add to each firing sequence 74 to provide a temporal placeholder for the firing sequence 74. Such dummy firings may help to maintain a consistent acoustic decay profile between each firing of a beam so that generation of artifacts associated with acoustic decay are limited. FIG. 7 shows an example when number of firings in a firing sequence is four, with the addition of an extra dummy firing. Additional dummy beams, such as a seventh 49 and eighth 51 dummy beams, are included in the example scanning sequence 70 depicted in FIG. 7. In addition, the fifth firing of each beam includes a dummy firing. Accordingly, a firing sequence, such as a ninth firing sequence 74, may include firing a fifth firing of beam A (a dummy firing), a forth firing of beam C, a third firing of a beam E, a second firing of a beam G, and a first firing of a beam I to achieve a firing number of five, including four normal firings and a one dummy firing.

Figure 8:
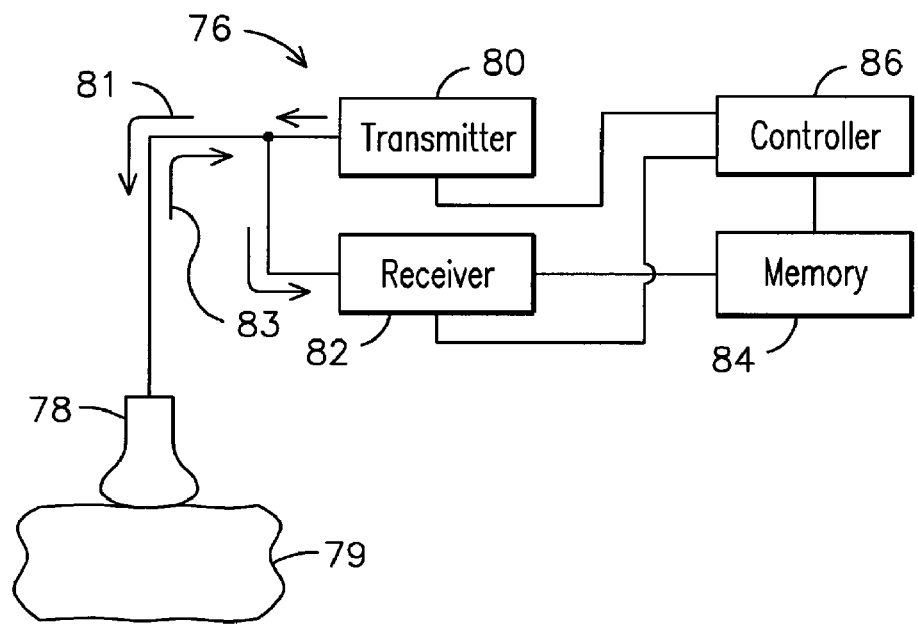
FIG. 8 shows a schematic diagram of an example system for performing a scanning sequence for an ultrasound scan according to an embodiment of the invention.

FIG. 8 shows a system 76 for performing a scanning sequence for an ultrasound scan, such as one or more of the example scanning sequences described above. The system 76 may include a transmitter 80 for transmitting ultrasound beams 81 to a subject 79 during an ultrasound scan. The system may also include a receiver 82 for receiving echo signals 83 from the subject 79 responsive to transmitted ultrasound beams 81. An ultrasound probe 78 may be configured for receiving the ultrasound beams 81 from the transmitter 80 and providing echo signals 83 from the subject 79 to the receiver 82. The system 76 may also include a memory 84 for storing information corresponding to the echo signals 83.

The system 76 may also include a controller 86 for performing a scanning sequence based on a processing of one or more parameters selected from the group consisting of the number of ultrasound beams, the pulse repetition interval, and the number of firings of the ultrasound beams. The processing of the one or more parameters by the controller 86 is configured to provide a continuous interleaving in the transmitted beams thereby avoiding a generation of beam interleaving discontinuities and a formation of artifacts in a resulting image. The controller 86 may be in communication with the transmitter 80 for controlling the transmitter 80 to perform the scanning sequence. The controller 86 may also be in communication with the receiver 82 to process received echo signals 83 according to the scanning sequence.

Figure 9:
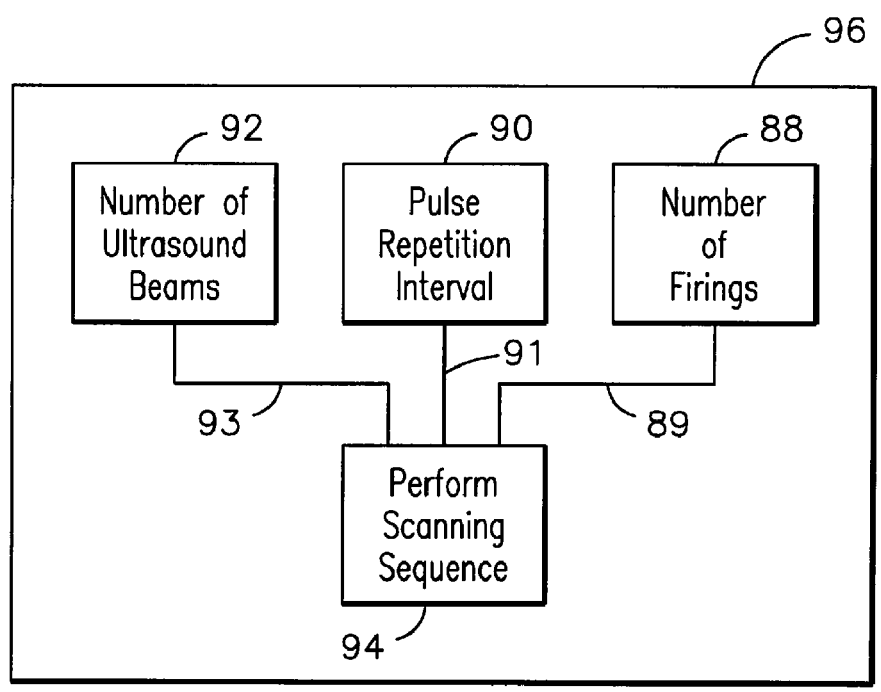
FIG. 9 shows a schematic diagram of an example apparatus for performing a scanning sequence for an ultrasound scan according to an embodiment of the invention.

In FIG. 9, an apparatus 96 for performing a scanning sequence for an ultrasound scan may include a first module 92 for establishing a number of ultrasound beams to be transmitted during an ultrasound scan, a second module 90 for establishing a pulse repetition interval to be used for performing the ultrasound scan, and a third module 88 for establishing a number of firings of each of the ultrasound beams to be performing during the ultrasound scan. The apparatus 86 may also include a fourth module 94 for performing a scanning sequence based on a processing of one or more parameters provided by the first 88, second 90, and third 92 modules, such as a number of ultrasound beams 93, a pulse repetition interval 91, and a number of firings of the ultrasound beams 89. The fourth module 94 may be configured to provide a continuous interleaving in the transmitted beams, thereby avoiding a generation of beam interleaving discontinuities and a formation of artifacts in a resulting image.

Based on the foregoing specification, the invention may be implemented using computer programming or engineering techniques including computer software, firmware, hardware or any combination or subset thereof, wherein the technical effect is to provide a continuous scanning sequence for ultrasound imaging. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

One skilled in the art of computer science will easily be able to combine the software created as described with appropriate general purpose or special purpose computer hardware, such as a microprocessor, to create a computer system or computer sub-system embodying the method of the invention. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention.

While certain embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method of performing a scanning sequence for an ultrasound scan in an ultrasound imaging system comprising:
    establishing a number of ultrasound beams to be transmitted by a transmitter during an ultrasound scan;
    establishing a number of firings of each of the ultrasound beams to be performed during the ultrasound scan; and
    transmitting scanning sequence based on the number of ultrasound beams and the number of firings such that a first firing for a first ultrasound beam occurs after a second firing of at least one other ultrasound beam within an interleaving group to provide a continuous interleaving in the transmitted beams.

2. The method of claim 1, wherein transmitting the scanning sequence comprises:
    establishing respective firing indices corresponding to the number of firings of each of the ultrasound beams; and
    controlling firing of each of the ultrasound beams according to the firing indices.

3. The method of claim 2, wherein controlling firing of each of the ultrasound beams comprises changing a firing index and an ultrasound beam to be fired for each firing to be performed.

4. The method of claim 3, wherein changing an ultrasound beam to be fired comprises changing to a different beam.

5. The method of claim 3, wherein changing the firing index comprises incrementing the firing index.

6. The method of claim 3, wherein changing the firing index comprises decrementing the firing index.

7. The method of claim 3, further comprising repeating the process of changing a firing index and an ultrasound beam to be fired until each firing index for each of the ultrasonic beams has been fired.

8. The method of claim 3, further comprising wrapping the scanning sequence from at least a first beam to be fired in a first frame to at least a second beam to be fired in a second frame.

9. The method of claim 2, further comprising arranging the scanning sequence into a plurality of firing sequences, each firing sequence comprising the number of firings.

10. The method of claim 9, further comprising resetting the firing index to the same index at the beginning of each respective firing sequence.

11. The method of claim 2, further comprising providing at least one dummy beam configured as a temporal place holder for the scanning sequence.

12. The method of claim 2, further comprising providing at least one dummy index for at least one of the firing indices for at least one of the ultrasonic beams configured as a temporal placeholder for the scanning sequence.

13. The method of claim 1, wherein the ultrasound scan is configured to obtain an image of tissue elasticity.

14. The method of claim 1, further comprising:
    establishing a pulse repetition interval to be used for performing the ultrasound scan, wherein the one or more parameters are selected from the group consisting of the number of ultrasound beams, the pulse repetition interval, and the number of firings of the ultrasound beams.

15. An apparatus for performing a scanning sequence for an ultrasound scan comprising:
    a first module for establishing a number of ultrasound beams to be transmitted during an ultrasound scan;
    a second module for establishing a pulse repetition interval to be used for performing the ultrasound scan;
    a third module for establishing a number of firings of each of the ultrasound beams to be performed during the ultrasound scan; and
    a fourth module for performing a scanning sequence based on the number of ultrasound beams and the number of firings such that a first firing for a first ultrasound beam occurs after a second firing of at least one other ultrasound beam within an interleaving group to provide a continuous interleaving in transmitted ultrasound beams.

16. A system for performing a scanning sequence for an ultrasound scan comprising:
    a transmitter for transmitting a plurality of ultrasound beams each comprising a plurality of firings to a subject during an ultrasound scan;
    a receiver for receiving echo signals from the subject responsive to transmitted ultrasound beams;
    a memory for storing information corresponding to the echo signals; and
    a controller for performing a scanning sequence based on the number of ultrasound beams and the number of firings such that a first firing for a first ultrasound beam occurs after a second firing of at least one other ultrasound beam within an interleaving group to provide a continuous interleaving in transmitted beams.

17. The method of claim 16, wherein the ultrasound beams are configured to obtain an image of tissue elasticity.

18. The system of claim 16, wherein the one or more parameters are selected from the group consisting of the number of ultrasound beams, the pulse repetition interval, and the number of firings of the ultrasound beams.

19. A non-transitory computer readable media containing program instructions, which when executed by one or more processors perform a scanning sequence for an ultrasound scan comprising:
    establishing a number of ultrasound beams to be transmitted during an ultrasound scan;
    establishing a number of firings of each of the ultrasound beams to be performed during the ultrasound scan; and
    performing a scanning sequence based on the number of ultrasound beams and the number of firings such that a first firing for a first ultrasound beam occurs after a second firing of at least one other ultrasound beam within an interleaving group to provide a continuous interleaving in the transmitted beams.

* * * * *

UNITED STATES PATENT AND TRADEMARK OFFICE
CERTIFICATE OF CORRECTION

| | | |
|---|---|---|
| PATENT NO. | : 7,846,099 B2 | Page 1 of 1 |
| APPLICATION NO. | : 11/551755 | |
| DATED | : December 7, 2010 | |
| INVENTOR(S) | : Lin et al. | |

It is certified that error appears in the above-identified patent and that said Letters Patent is hereby corrected as shown below:

In Column 8, Line 40, in Claim 17, delete "method" and insert -- system --, therefor.

Signed and Sealed this
Nineteenth Day of April, 2011

David J. Kappos
*Director of the United States Patent and Trademark Office*